(12) United States Patent
Foster et al.

(10) Patent No.: US 11,992,676 B2
(45) Date of Patent: *May 28, 2024

(54) STIMULATION/SENSING ELECTRODE FIXATION DEVICE AND ELECTRICAL LEAD

(71) Applicant: Cardiac Pacemakers Inc., St. Paul, MN (US)

(72) Inventors: Arthur J. Foster, Blaine, MN (US); Benjamin J. Haasl, Forest Lake, MN (US); Linda L. Evert, Circle Pines, MN (US); G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/853,271

(22) Filed: Jun. 29, 2022

(65) Prior Publication Data

US 2022/0323749 A1  Oct. 13, 2022

Related U.S. Application Data

(63) Continuation of application No. 16/038,938, filed on Jul. 18, 2018, now Pat. No. 11,464,967.
(Continued)

(30) Foreign Application Priority Data

Sep. 19, 2017 (NL) ...................................... 2019577

(51) Int. Cl.
*A61N 1/05* (2006.01)
*A61N 1/375* (2006.01)
(Continued)

(52) U.S. Cl.
CPC ........... *A61N 1/0573* (2013.01); *A61N 1/375* (2013.01); *A61N 1/36114* (2013.01); *A61N 1/362* (2013.01); *A61N 1/3684* (2013.01)

(58) Field of Classification Search
CPC .. A61N 1/0573; A61N 1/375; A61N 1/36114; A61N 1/3684
See application file for complete search history.

(56) References Cited

U.S. PATENT DOCUMENTS

| 4,214,804 A | 7/1980 | Little |
| 4,886,074 A | 12/1989 | Bisping |

(Continued)

FOREIGN PATENT DOCUMENTS

WO 2004/069329 A1 8/2004

OTHER PUBLICATIONS

International Search Report and Written Opinion issued in PCT/US2019/028302, dated Jul. 19, 2019, 12 pages.

(Continued)

*Primary Examiner* — Rex R Holmes
*Assistant Examiner* — Jennifer L Ghand
(74) *Attorney, Agent, or Firm* — Nelson Mullins Riley & Scarborough LLP

(57) ABSTRACT

A device for the active fixation of an implantable medical lead includes a housing, a tine assembly, and rotatable shaft. The housing includes a proximal end for connecting to the lead and a distal end opposite the proximal end. The housing defines a housing lumen having a longitudinal axis extending between the proximal end and the distal end. The tine assembly is disposed within the housing lumen. The tine assembly includes at least one tine configured to self-bias from a linear configuration within the housing to a curved configuration outside of the housing. The rotatable shaft extends through the housing lumen. The shaft is configured (Continued)

to engage the tine assembly such that rotation of the shaft transitions the at least one tine between the linear configuration and the curved configuration.

16 Claims, 7 Drawing Sheets

Related U.S. Application Data

(60) Provisional application No. 62/534,584, filed on Jul. 19, 2017.

(51) Int. Cl.
    *A61N 1/36*     (2006.01)
    *A61N 1/362*     (2006.01)
    *A61N 1/368*     (2006.01)

(56) References Cited

U.S. PATENT DOCUMENTS

| | | | |
|---|---|---|---|
| 5,095,916 A | 3/1992 | Smits | |
| 5,353,800 A | 10/1994 | Pohndorf et al. | |
| 5,476,500 A * | 12/1995 | Fain | A61N 1/0563 |
| | | | 600/375 |
| 5,492,119 A | 2/1996 | Abrams | |
| 5,683,447 A * | 11/1997 | Bush | A61N 1/056 |
| | | | 607/126 |
| 6,704,605 B2 | 3/2004 | Soltis et al. | |
| 6,931,286 B2 | 8/2005 | Sigg et al. | |
| 7,044,934 B2 | 5/2006 | Mickley | |
| 7,177,704 B2 | 2/2007 | Laske et al. | |
| 7,212,870 B1 | 5/2007 | Helland | |
| 7,212,871 B1 | 5/2007 | Morgan | |
| 7,319,905 B1 | 1/2008 | Morgan et al. | |
| 7,369,901 B1 | 5/2008 | Morgan et al. | |
| 7,418,298 B2 | 8/2008 | Shiroff et al. | |
| 7,433,739 B1 | 10/2008 | Salys et al. | |
| 7,496,410 B2 | 2/2009 | Heil, Jr. | |
| 7,546,166 B2 | 6/2009 | Michels et al. | |
| 7,657,326 B2 | 2/2010 | Bodner et al. | |
| 7,711,437 B1 | 5/2010 | Bornzin et al. | |
| 7,751,905 B2 | 7/2010 | Feldmann et al. | |
| 7,860,581 B2 | 12/2010 | Eckerdal et al. | |
| 7,920,927 B2 | 4/2011 | Zarembo et al. | |
| 7,920,928 B1 | 4/2011 | Yang et al. | |
| 8,000,805 B2 | 8/2011 | Swoyer et al. | |
| 8,036,756 B2 | 10/2011 | Swoyer et al. | |
| 8,036,757 B2 | 10/2011 | Worley | |
| 8,090,451 B2 | 1/2012 | Tyson, Jr. | |
| 8,346,374 B2 | 1/2013 | Foster et al. | |
| 8,406,899 B2 | 3/2013 | Reddy et al. | |
| 9,008,768 B2 | 4/2015 | Zhu et al. | |
| 9,302,098 B2 | 4/2016 | Zhang et al. | |
| 9,545,513 B2 | 1/2017 | Hastings et al. | |
| 9,579,501 B2 | 2/2017 | Shuros et al. | |
| 9,844,663 B2 * | 12/2017 | Swaminathan | A61N 1/057 |
| 11,318,303 B2 * | 5/2022 | Shuros | A61N 1/059 |
| 11,464,967 B2 * | 10/2022 | Foster | A61N 1/0573 |
| 11,517,747 B2 | 12/2022 | Foster et al. | |
| 11,666,753 B2 * | 6/2023 | Shuros | A61N 1/0573 |
| | | | 607/128 |
| 2003/0204233 A1 | 10/2003 | Laske et al. | |
| 2004/0054388 A1 | 3/2004 | Osypka | |
| 2004/0215307 A1 | 10/2004 | Michels et al. | |
| 2005/0113900 A1 | 5/2005 | Shiroff et al. | |
| 2006/0106315 A1 | 5/2006 | Edens | |
| 2006/0129218 A1 | 6/2006 | Swoyer et al. | |
| 2006/0155353 A1 | 7/2006 | Heil | |
| 2007/0050003 A1 | 3/2007 | Zarembo et al. | |
| 2007/0050004 A1 | 3/2007 | Swoyer et al. | |
| 2007/0106202 A1 | 5/2007 | Salo et al. | |
| 2007/0129782 A1 | 6/2007 | Feldmann et al. | |
| 2007/0239241 A1 | 10/2007 | Tyson | |
| 2008/0065185 A1 | 3/2008 | Worley | |
| 2008/0109042 A1 | 5/2008 | Bodner et al. | |
| 2008/0249596 A1 | 10/2008 | Shiroff et al. | |
| 2008/0262588 A1 | 10/2008 | Zarembo et al. | |
| 2008/0288040 A1 | 11/2008 | Eckerdal et al. | |
| 2009/0259272 A1 | 10/2009 | Reddy et al. | |
| 2010/0305670 A1 | 12/2010 | Hall et al. | |
| 2010/0324644 A1 | 12/2010 | Levi et al. | |
| 2011/0009939 A1 | 1/2011 | Foster et al. | |
| 2011/0160817 A1 | 6/2011 | Foster et al. | |
| 2011/0199173 A1 | 8/2011 | Leijssen et al. | |
| 2011/0251662 A1 | 10/2011 | Griswold et al. | |
| 2012/0004714 A1 | 1/2012 | Kleve et al. | |
| 2012/0165914 A1 * | 6/2012 | Walker | A61N 1/0575 |
| | | | 607/119 |
| 2012/0179221 A1 | 7/2012 | Reddy et al. | |
| 2013/0261689 A1 | 10/2013 | Zhu et al. | |
| 2013/0296852 A1 | 11/2013 | Madjarov et al. | |
| 2014/0067036 A1 | 3/2014 | Shuros et al. | |
| 2014/0107755 A1 | 4/2014 | Ollivier | |
| 2014/0207149 A1 | 7/2014 | Hastings et al. | |
| 2014/0243946 A1 | 8/2014 | Zhang et al. | |
| 2015/0080995 A1 | 3/2015 | Seeley et al. | |
| 2015/0105729 A1 | 4/2015 | Valeti et al. | |
| 2015/0313669 A1 | 11/2015 | Darmos et al. | |
| 2016/0331957 A1 | 11/2016 | Gindele et al. | |
| 2017/0043158 A1 | 2/2017 | Kelly et al. | |
| 2017/0106185 A1 | 4/2017 | Orts et al. | |
| 2019/0022379 A1 | 1/2019 | Foster et al. | |
| 2019/0321625 A1 | 10/2019 | Shuros et al. | |
| 2020/0114146 A1 | 4/2020 | Foster et al. | |
| 2022/0211998 A1 | 7/2022 | Shuros et al. | |

OTHER PUBLICATIONS

International Search Report and Written Opinion issued in PCT/US2019/056095, dated Jan. 28, 2020, 14 pages.
Search Report and Written Opinion issued in NL Application 2019577, dated Mar. 1, 2018, 7 pages.

* cited by examiner

STIMULATION/SENSING ELECTRODE FIXATION DEVICE AND ELECTRICAL LEAD

CROSS-REFERENCE TO RELATED APPLICATION

This application is a Continuation of U.S. patent application Ser. No. 16/038,938 filed on Jul. 18, 2018, which claims priority to U.S. Provisional Application No. 62/534,584, filed Jul. 19, 2017, and Netherlands Application No. 2019577, filed Sep. 19, 2017, both of which are herein incorporated by reference in their entireties.

TECHNICAL FIELD

The present invention relates to medical devices and methods for the active fixation of an implantable medical lead. More specifically, the invention relates to devices and methods for active fixation of implantable medical leads for mapping and stimulating the bundle of His in a patient's heart.

BACKGROUND

Cardiac rhythm management systems are useful for electrically stimulating a patient's heart to treat various cardiac arrhythmias. A method of electrically stimulating the heart can include stimulating the His bundle at a location proximate to the tricuspid valve at the interatrial septum in the right atrium of the heart or at a location proximate to the tricuspid valve at the interventricular septum in the right ventricle of the heart. Directly stimulating the bundle of His can simultaneously pace both the right and left ventricles of the heart, potentially avoiding pacing induced dyssynchrony which may occur with right ventricular apex pacing. There is a continuing need for improved His bundle lead designs and assemblies.

SUMMARY

Example 1 is a device for the active fixation of an implantable medical lead. The device includes a housing, a tine assembly, an electrode, and rotatable shaft. The housing includes a proximal end for connecting to the lead and a distal end opposite the proximal end. The housing defines a housing lumen having a longitudinal axis extending between the proximal end and the distal end. The tine assembly is disposed within the housing lumen. The tine assembly includes at least one tine configured to self-bias from a linear configuration within the housing to a curved configuration outside of the housing. The electrode is disposed at the distal end of the housing. The rotatable shaft is connected to the electrode and extends through the housing lumen. The shaft is configured to engage the tine assembly such that rotation of the shaft transitions the at least one tine between the linear configuration and the curved configuration.

Example 2 is the device of Example 1, wherein the housing further includes internal screw threads extending along the housing lumen, and the tine assembly further includes a driver member and a carrier member. The driver member is disposed within the housing lumen. The driver member defines a driver lumen that is coaxial with the housing lumen. The driver member includes a threaded portion having external screw threads engaged with the internal screw threads of the housing, a flange, and a hub connecting the flange to the threaded portion. The carrier member is rotatably disposed around the hub of the driver member. The at least one tine is connected to and projecting from the carrier member. The rotatable shaft extends through the driver lumen. The shaft is configured to engage the driver member such that rotation of the shaft rotates the driver member to transition the at least one tine between the linear configuration and the curved configuration.

Example 3 is the device of Example 2, wherein the flange and the threaded portion of the driver member constrain axial movement of the carrier member.

Example 4 is the device of either of Examples 2 or 3, wherein the housing further defines at least one slot at least partially radially outward from the internal screw threads, the at least one slot extending from the proximal end to the distal end and parallel to the longitudinal axis.

Example 5 is the device of Example 4, wherein the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

Example 6 is the device of any of Examples 2-5, wherein the driver lumen is sized so that the driver member can slide along the shaft while the shaft rotates the driver member.

Example 7 is the device of any of Examples 1-6, wherein rotation of the shaft in a first direction moves the at least one tine out of the housing lumen, transitioning the at least one tine from the linear configuration to the curved configuration to fix the lead to tissue, and rotation of the shaft in a second direction opposite the first direction retracts the at least one tine into the housing lumen, transitioning the at least one tine from the curved configuration to the linear configuration.

Example 8 is the device of any of Examples 1-7, wherein the at least one tine is conductive and the electrode and the shaft are electrically insulated from the at least one tine.

Example 9 is the device of any of Examples 1-8, wherein the at least one tine includes a plurality of tines.

Example 10 is the device of any of Examples 1-9, wherein the electrode includes a conical tip having an axis that is collinear with the longitudinal axis of the housing lumen.

Example 11 is the device of any of Examples 1-10, wherein the shaft is electrically and mechanically connected to the electrode.

Example 12 is an implantable medical lead including a flexible, tubular lead body including a proximal end and a distal end, a connector assembly disposed at the proximal end, an electrical conductor extending from the connector assembly to the distal end, and a device for the active fixation of the implantable medical lead according to any of Examples 1-11. The device is disposed at the distal end of the lead body. The electrical conductor is mechanically and electrically connected to the shaft.

Example 13 is a method of making a device for the active fixation of an implantable medical lead. The method includes attaching at least one tine to a carrier member, inserting a hub extending from a threaded portion of a driver member through the carrier member such that the carrier member is rotatable about the hub, forming a flange at an end of the hub opposite the threaded portion of the driver member, inserting the at least one tine into a proximal end of a longitudinal slot of a housing lumen of a housing to place the at least one tine in a linear configuration contained by the housing, threading the threaded portion of the drive member into a threaded portion at a proximal end of the housing, inserting a shaft through the a driver lumen of the driver member at the proximal end of the housing and through the housing lumen to a distal end of the housing, and connecting an electrode to the shaft at the distal end of the housing. The tine is self-biasing to a curved configuration. The flange and the threaded portion of the driver member restrain the axial movement of the carrier member.

Example 14 is the method of Example 13, further including placing a seal around the shaft at the distal end of the housing before connecting the electrode to the shaft.

Example 15 is the method of either of Examples 13 or 14, wherein forming the flange at the end of the hub includes heating the end of the hub until it softens and flanging the heated hub outward to form the flange.

Example 16 is a device for the active fixation of an implantable medical lead into tissue. The device includes a housing, a tine assembly, and a rotatable shaft. The housing includes a proximal end for connecting to the lead and a distal end opposite the proximal end. The housing defines a housing lumen having a longitudinal axis extending between the proximal end and the distal end. The tine assembly is disposed within the housing lumen. The tine assembly includes at least one tine configured to self-bias from a linear configuration within the housing to a curved configuration outside of the housing. The rotatable shaft extends through the housing lumen. The shaft is configured to engage the tine assembly such that rotation of the shaft transitions the at least one tine between the linear configuration and the curved configuration.

Example 17 is the device of Example 16, wherein rotation of the shaft in a first direction moves the at least one tine out of the housing lumen, transitioning the at least one tine from the linear configuration to the curved configuration to fix the lead to tissue, and rotation of the shaft in a second direction opposite the first direction retracts the at least one tine into the housing lumen, transitioning the at least one tine from the curved configuration to the linear configuration to release the lead from tissue.

Example 18 is the device of either of Examples 16 or 17, wherein the at least one tine includes a plurality of tines.

Example 19 is the device of any of Examples 16-18, further including an electrode disposed at the distal end of the housing, the rotatable shaft connected to the electrode Example 20 is the device of Example 19, wherein the electrode includes a conical tip having an axis that is collinear with the longitudinal axis of the housing lumen.

Example 21 is the device of either of Examples 19-20, wherein the shaft is electrically and mechanically connected to the electrode.

Example 22 is the device of any of Examples 16-21, wherein the housing further includes internal screw threads extending along the housing lumen, and the tine assembly further includes a drive member and a carrier member. The driver member is disposed within the housing lumen. The driver member defines a driver lumen that is coaxial with the housing lumen. The driver member includes a threaded portion having external screw threads engaged with the internal screw threads of the housing, a flange, and a hub connecting the flange to the threaded portion. The carrier member is rotatably disposed around the hub of the driver member. The at least one tine is connected to and projecting from the carrier member. The rotatable shaft extends through the driver lumen. The shaft is configured to engage the driver member such that rotation of the shaft rotates the driver member to transition the at least one tine between the linear configuration and the curved configuration.

Example 23 is the device of Example 22, wherein the flange and the threaded portion of the driver member constrain axial movement of the carrier member.

Example 24 is the device of either of Examples 22 or 23, wherein the housing further defines at least one slot at least partially radially outward from the internal screw threads, the at least one slot extending from the proximal end to the distal end and parallel to the longitudinal axis.

Example 25 is the device of Example 24, wherein the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

Example 26 is the device of any of Examples 22-25, wherein the driver lumen is sized so that the driver member can slide along the shaft while the shaft rotates the driver member.

Example 27 is an implantable medical lead including a flexible, tubular lead body including a proximal end and a distal end, a connector assembly connector disposed at the proximal end, an electrical conductor extending through the tubular body from the connector assembly to the distal end, and a device for the active fixation of the implantable medical lead. The device is disposed at the distal end of the lead. The device includes a housing, a tine assembly, an electrode, and a rotatable shaft. The housing includes a proximal end for connecting to the distal end of the lead body and a distal end opposite the proximal end. The housing defines a housing lumen having a longitudinal axis extending between the proximal end and the distal end. The tine assembly is disposed within the housing lumen. The tine assembly includes at least one tine configured to self-bias from a linear configuration within the housing to a curved configuration outside of the housing. The electrode is disposed at the distal end of the housing. The rotatable shaft is connected to the electrode and extends through the housing lumen. The shaft is configured to engage the tine assembly such that rotation of the shaft transitions the at least one tine between the linear configuration and the curved configuration. The shaft mechanically and electrically connects the electrical conductor to the electrode.

Example 28 is the lead of Example 27, wherein the at least one tine is conductive and the electrode and the shaft are electrically insulated from the at least one tine.

Example 29 is the lead of Example 28, further including at least one tine conductor extending through the tubular body from the connector assembly to the at least one tine.

Example 30 is the lead of any of Examples 27-29, wherein the housing further includes internal screw threads extending along the housing lumen, and the tine assembly further includes a driver member and a carrier member. The driver member is disposed within the housing lumen. The driver member defines a driver lumen that is coaxial with the housing lumen. The driver member includes a threaded portion having external screw threads engaged with the internal screw threads of the housing, a flange, and a hub connecting the flange to the threaded portion. The carrier member is rotatably disposed around the hub of the driver member. The at least one tine is connected to and projects from the carrier member. The rotatable shaft extends through the driver lumen. The shaft is configured to engage the driver member such that rotation of the shaft rotates the driver member to transition the at least one tine between the linear configuration and the curved configuration. The flange and the threaded portion of the driver member constrain axial movement of the carrier member.

Example 31 is the lead of Example 30, wherein the housing further defines at least one slot at least partially radially outward from the internal screw threads. The at least one slot extends from the proximal end to the distal end and parallel to the longitudinal axis. The carrier member includes at least one lobe configured to engage the at least one slot to prevent axial rotation of the carrier member relative to the housing while permitting the carrier member to move through the housing lumen while the shaft rotates the driver member. The at least one tine is connected to and projects from the at least one lobe.

Example 32 is a method of making a device for the active fixation of an implantable medical lead. The method includes attaching at least one tine to a carrier member, inserting a hub extending from a threaded portion of a driver member through the carrier member such that the carrier member is rotatable about the hub, forming a flange at an end of the hub opposite the threaded portion of the driver member, inserting the at least one tine into a proximal end of a longitudinal slot of a housing lumen of a housing to place the at least one tine in a linear configuration contained by the housing, threading the threaded portion of the drive member into a threaded portion at a proximal end of the housing, inserting a shaft through the a driver lumen of the driver member at the proximal end of the housing and through the housing lumen to a distal end of the housing, and connecting an electrode to the shaft at the distal end of the housing. The flange and the threaded portion of the driver member restraining the axial movement of the carrier member. The tine self-biasing to a curved configuration.

Example 33 is the method of Example 32, further including placing a seal around the shaft at the distal end of the housing before connecting the electrode to the shaft.

Example 34 is the method of either of Examples 32 or 33, wherein forming the flange at the end of the hub includes heating the end of the hub until it softens and flanging the heated hub outward to form the flange.

Example 35 is the method of either of Examples 32 or 33, wherein forming the flange at the end of the hub includes connecting the flange to the end of the hub.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
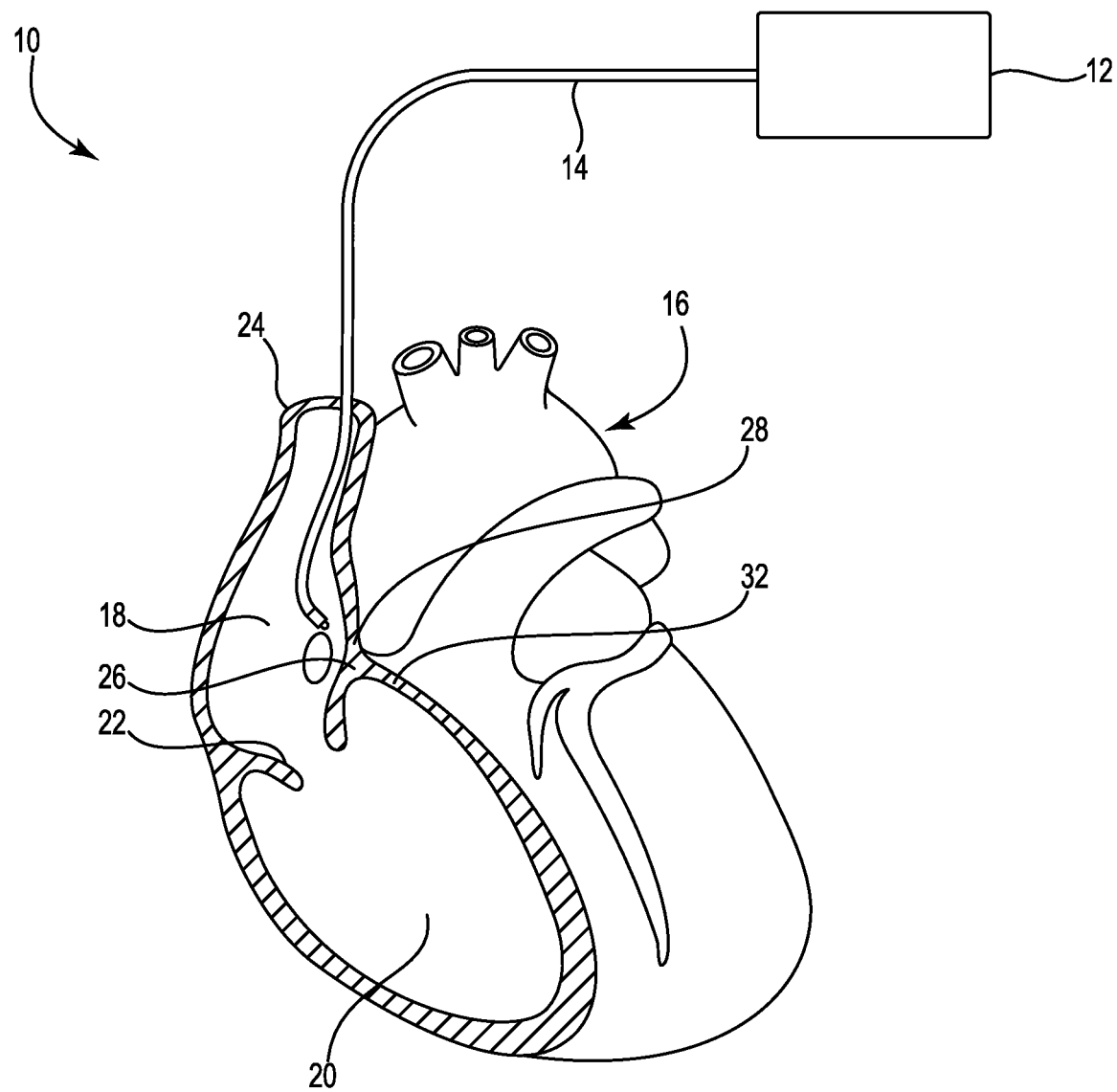
FIG. 1 is a schematic view of system for mapping and stimulating the bundle of His in a patient's heart, including a lead according to embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of system 10 for mapping and stimulating the bundle of His, according to embodiments of this disclosure. As shown in FIG. 1, the system 10 includes an implantable pulse generator 12 coupled to a lead 14 deployed in a patient's heart 16. The pulse generator 12 generates an electrical pacing stimulus to be delivered to the heart 16. The lead 14 operates to convey electrical signals and stimuli between the heart 16 and the pulse generator 12. As further shown in FIG. 1, the heart 16 includes a right atrium 18 and a right ventricle 20 separated by a tricuspid valve 22. In the embodiment shown in FIG. 1, the lead 14 enters the vascular system through a vascular entry site (not shown) and a superior vena cava 24 to be implanted in the right atrium 18. The bundle of His 26 can be stimulated at an atrial location proximate to the tricuspid valve 22 at an interatrial septum 28 in the right atrium 18, as shown in FIG. 1. This location is proximate to the apex of the triangle of Koch. Alternatively, the bundle of His 24 can be stimulated at a ventricular location proximate to the tricuspid valve 22 at an interventricular septum 32 in the right ventricle 20 by passing the lead 14 through the tricuspid valve 22 and into the right ventricle 20.

The system 10 allows direct therapeutic stimulation of the bundle of His 26 by fixating the lead 14 at one of the locations describe above. Mapping at one of the locations described above is necessary to be able to position the lead 14 close enough to the bundle of His 26 for efficient and effective pacing. Some prior art leads rely on non-contact sensing or surface contact sensing with electrodes to map the location of the bundle of His 26. However, in some instances, this may not be accurate enough to identify the proper location to implant the lead 14. Such precise mapping can require repeated penetration of the myocardium to achieve the sensitivity necessary to accurately locate the bundle of His 26. In some other prior art leads, a helical electrode can be employed to repeatedly penetrate the myocardium to locate the bundle of His 26. However, repeatedly implanting and removing the helical electrode, which requires multiple rotations of the helical electrode, can be time consuming and may damage the myocardium. In addition, once a suitable location is found, the recoil from the force required to implant the helical electrode to fixate the prior art lead can result in the helical electrode moving from the identified location and being implanted in a less suitable location. Embodiments of the present disclosure permit mapping that is faster and less harmful to the myocardium, while employing a fixation device that accurately secures a lead electrode in the myocardium.

Figure 2:
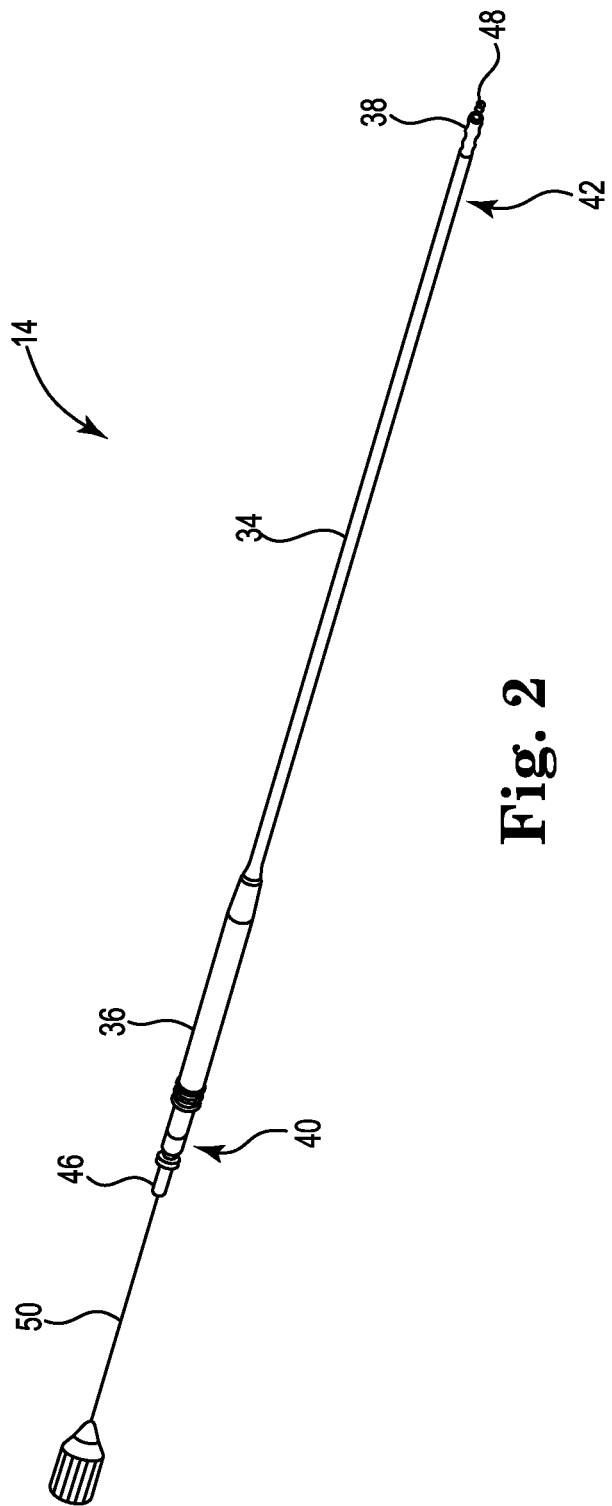
FIG. 2 is a perspective view of the lead of FIG. 1, according to embodiments of this disclosure.

FIG. 2 is a perspective view of the lead 14 of FIG. 1, according to embodiments of this disclosure. As shown in FIG. 2, the lead 14 includes a lead body 34, a connector assembly 36, and a fixation device 38. The lead body 34 is a flexible tubular body including a proximal end 40 and a distal end 42, and containing an electrical conductor 44 (FIG. 3) extending from the proximal end 40 to the distal end 42. The connector assembly 36 is disposed at the proximal end 40 and includes a terminal pin 46 mechanically and electrically connected to the electrical conductor 44. The connector assembly 36 is configured to mechanically and electrically couple the lead 14 to the pulse generator 12 (FIG. 1). The fixation device 38 is a device for the active fixation of the lead 14. The fixation device 38 is disposed at the distal end 42 of the lead 14 and includes an electrode 48. In the embodiment of FIG. 2, the electrical conductor 44 is electrically connected to the electrode 48 so that it can function as an active electrode to stimulate the bundle of His 26 (FIG. 1).

In some embodiments, the electrical conductor 44 is a coil conductor and the fixation device 38 is configured such that rotation of the terminal pin 46 rotates the electrical conductor 44 to cause the fixation device 38 to fixate the lead 14, as described below. In some embodiments, a stylet 50 can be extended through connector assembly 36 and the lead body 34 to the fixation device 38 and engage the fixation device 38 such that rotation of the stylet 50 causes the fixation device 38 to fixate the lead 14, as described below.

Figure 3:
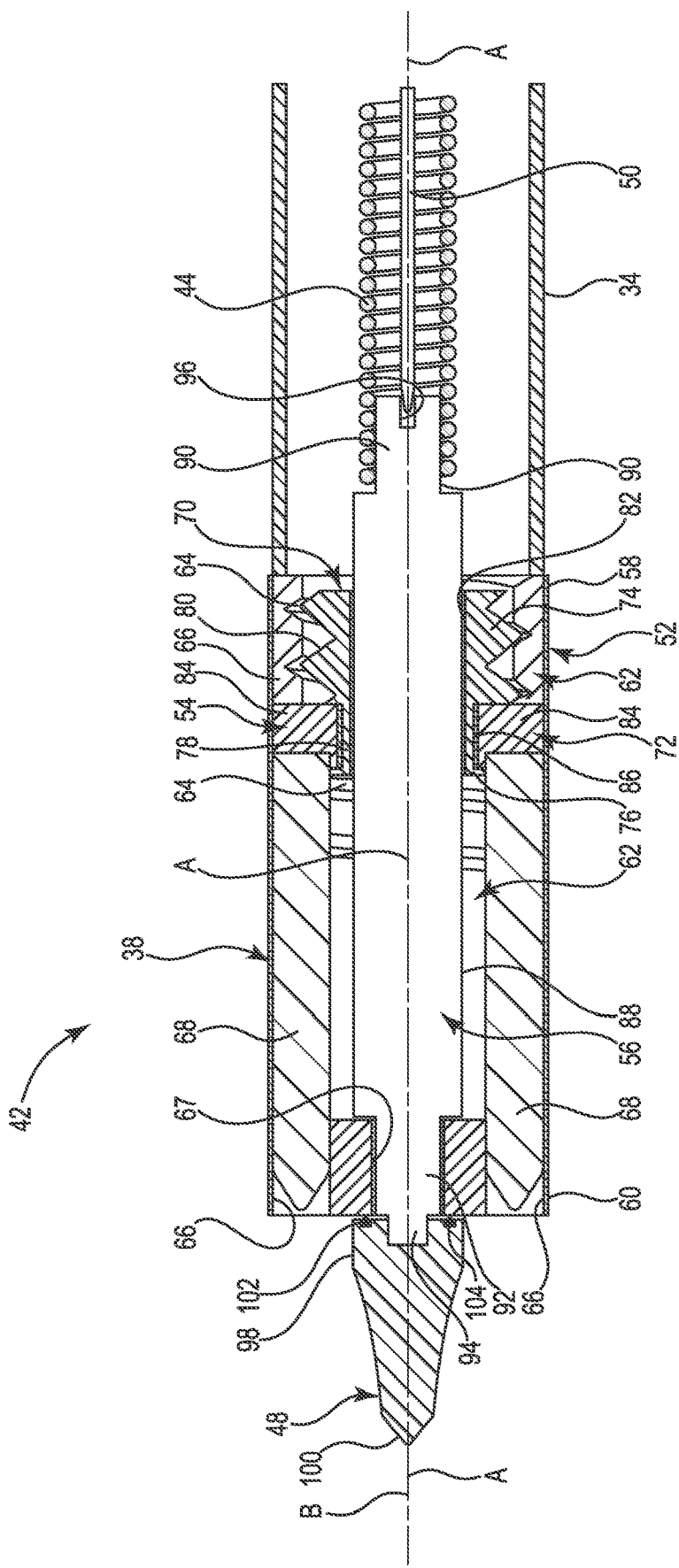
FIG. 3 is schematic cross-sectional view of a distal end of the lead of FIG. 2 showing a device for the active fixation of the lead in an undeployed state, according to embodiments of this disclosure.
Figure 4:
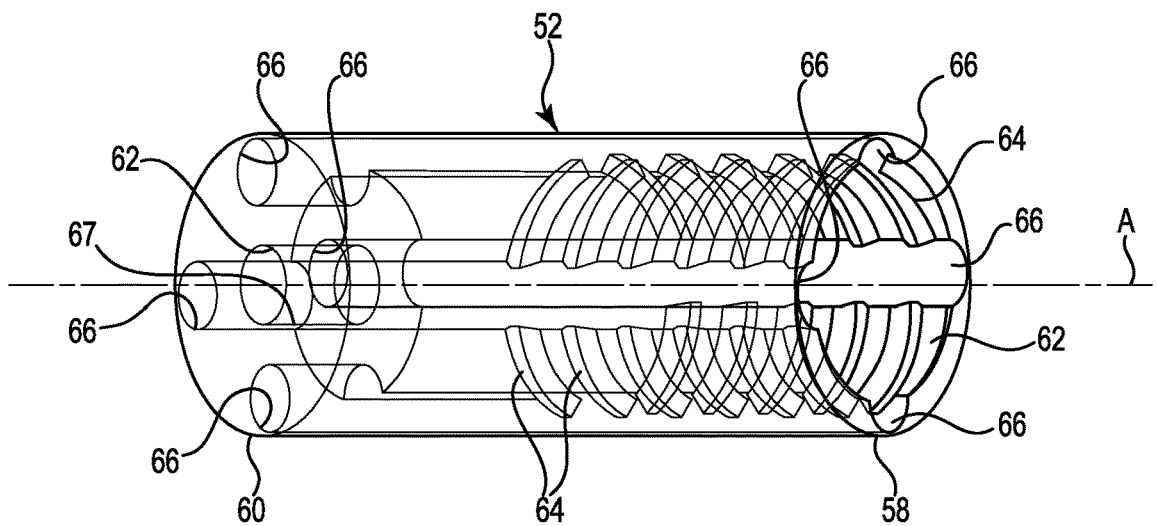
FIG. 4 is a transparent perspective view of a housing of the fixation device of FIG. 3 for the active fixation of the lead, according to embodiments of this disclosure.

FIG. 3 is schematic cross-sectional view of the distal end 42 of the lead 14 of FIG. 2 including the fixation device 38, according to embodiments of this disclosure. In FIG. 3, the fixation device 38 is shown in an undeployed stated. As shown in FIG. 3, in addition to the electrode 48, the fixation device 38 can further include a housing 52, a tine assembly 54, and a rotatable shaft 56. FIG. 4 is a transparent perspective view of the housing 52 of the fixation device 38 of FIG. 3, according to embodiments of this disclosure. Considering FIGS. 3 and 4 together, the housing 52 can include a proximal end 58 and a distal end 60 opposite the proximal end 58. The housing 52 can define a housing lumen 62, internal screw threads 64, and at least one slot 66 (two shown in FIG. 3, four shown in FIG. 4). The housing lumen 62 can include a narrow portion 67 at the distal end 60 and have a longitudinal axis A extending between the proximal end 58 and the distal end 60 of the housing 52. The internal screw threads 64 can extend along a portion of the housing lumen 62 from the proximal end 58 of the housing 52. The at least one slot 66 is formed at least partially radially outward from the internal screw threads 64 and extends longitudinally from the proximal end 58 to the distal end 60 of the housing 52 and is parallel to the longitudinal axis A. The housing 52 can be made of a biocompatible polymer that is rigid at body temperature, such as polyetheretherketone (PEEK) or polyethersulfone (PES). The housing 52 can be formed by, for example, molding, machining, or 3D additive manufacturing.

Figure 5:
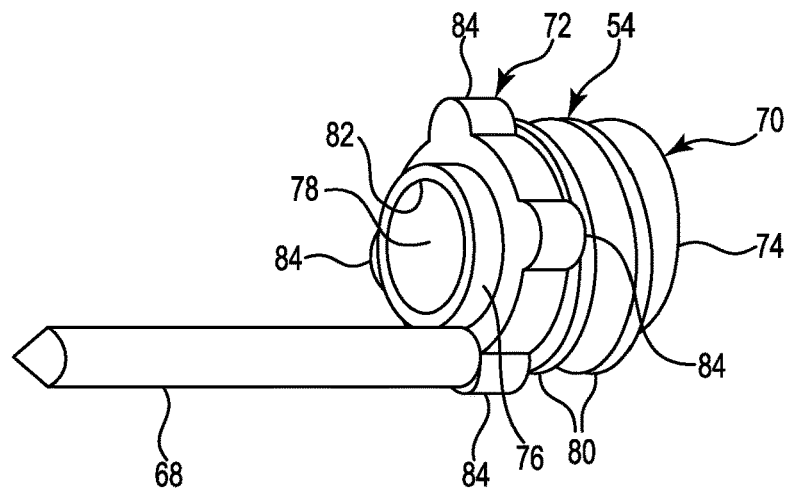
FIG. 5 is a perspective view of some of a tine assembly of FIG. 3 for the active fixation of the lead, according to embodiments of this disclosure.

FIG. 5 is a perspective view the tine assembly 54 of FIG. 3, according to embodiments of this disclosure. Considering FIGS. 3 and 5 together, the tine assembly 54 can include at least one tine 68, a driver member 70, and a carrier member 72. The embodiment of FIGS. 3 and 5 includes four tines 68 (FIG. 7), two shown in FIG. 3, one shown in FIG. 5 with the remaining three omitted for clarity. The at least one tine 68 is formed of a material having a shape memory, for example nitinol or a gold/stainless steel alloy, such that the at least one tine 68 can biased to be curved configuration when unrestrained and outside of the housing 52 (FIG. 7) and can be in a linear configuration when restrained by the housing 52, as shown in FIGS. 3 and 5. The at least one tine 68 can be pointed for ease in entering tissue for fixation.

The driver member 70 can include a threaded portion 74, a flange 76, and a hub 78. The threaded portion 74 includes external screw threads 80 for threaded engagement with the internal screw threads 64 of the housing 52. The hub 78 connects the flange 76 to the threaded portion 74. The flange 76 extends radially outward from the hub 78. The driver member 70 can also define a driver lumen 82 extending through the threaded portion 74, the hub 78 and the flange 76. The driver lumen 82 can be coaxial with the housing lumen 62 as shown in FIG. 3.

In some embodiments, such as the embodiment shown in FIG. 3, the driver member 70 can be a one-piece, monolithic structure. In such embodiments, the flange 76 can be formed shaping, or flanging, an end of the hub 78 opposite the threaded portion 74 radially outward to form the flange 76. In some embodiments, the end of the hub 78 may need to be heated until it softens, before flanging the heated end of the hub 78 outward to form the flange 76. In other embodiments, the driver member 70 can be a two-piece structure in which the flange 76 and the hub 78 may be a single piece that connects to the threaded portion 74 by, for example, a snap joint or an adhesive joint. Alternatively, the hub 78 and the threaded portion 74 may be a single piece that connects to the flange 76 by, for example, an adhesive joint or a weld.

The driver member 70 can be made of a biocompatible metal, such as stainless steel, Elgiloy, MP35N, or titanium, or a biocompatible polymer that is rigid at body temperature, such as polyetheretherketone (PEEK) or polyethersulfone (PES), or a combination of any of the foregoing materials. The driver member 70 can be formed by, for example, molding, machining, or 3D additive manufacturing. In some embodiments, should the at least one tine 68 and the driver member 70 be formed of conductive materials, the flange 76 can be adequately spaced from the at least one tine 68 so that the electrode 48 and the shaft 56 are electrically insulated from the at least one tine 68. In some embodiments in which the driver member 70 is a two-piece structure, the threaded portion 74 can be formed of a metal while the flange 76 is formed of a non-conductive polymer to maintain electrical isolation between the shaft 56 and the at least one tine 68.

The carrier member 72 can include at least one lobe 84 (two shown in FIG. 3, four in the embodiment of FIG. 3, as shown in FIG. 5) at a circumference of the carrier member 72. The at least one tine 68 can be attached to, and project from the at least one lobe 84. In the embodiment of FIGS. 3 and 5, each of the four tines 68 is attached to one of the four lobes 84. The tines 68 can be attached by, for example, molding the lobes 84 around the tines 68, as shown in FIG. 3. Alternatively, the tines 68 can be attached to the lobes 84 by a mechanical fastener, adhesive, or other suitable means. The carrier member 72 can define a carrier lumen 86 through which the hub 78 passes. An inner diameter of the carrier lumen 86 is sufficiently larger than an outer diameter of the hub 78 such that the carrier member 72 is rotatably disposed around the hub 78. As shown in FIG. 3, so configured, the flange 76 and the threaded portion 74 constrain the movement of the carrier member 72 in the axial direction, but not so tightly as to prevent or interfere with the ability of the carrier member 72 to rotate relative to the hub 78.

The carrier member 72 can be made of a biocompatible polymer that is rigid at body temperature and will thread well through the housing 52 without sticking, such as polyoxymethylene (POM) or polyetheretherketone (PEEK). The carrier member 72 can be formed by, for example, molding, machining, or 3D additive manufacturing.

As shown in FIG. 3, the rotatable shaft 56 can be a one-piece structure including a main shaft portion 88, a proximal shaft portion 90 on a proximal end of the main shaft portion 88, a distal shaft portion 92 on a distal end of the main shaft portion 88, and an electrode shaft portion 94 extending distally from the distal shaft portion 92. The shaft 56 extends through the housing 52. In some embodiments, at least a portion of main shaft portion 88 and the proximal shaft portion 90 extend proximally from the proximal end 58 of the housing 52. In the embodiment shown in FIG. 3, the electrical conductor 44 is mechanically and electrically connected to the proximal shaft portion 90. The electrode shaft portion 94 extends distally from the distal end 60 of the housing 52. The distal shaft portion 92 is narrower than a diameter of the narrow portion 67 of the housing lumen 62, and the main shaft portion 88 is wider than the narrow portion 67, to limit the movement of the shaft 56 in the direction of the distal end 60. In some embodiments, the proximal shaft portion 90 can include a stylet engagement structure 96 so that the stylet 50 can engage the fixation device 38, as shown in FIG. 3. The stylet engagement structure 96 can be a slot, as shown, to engage a flat-bladed stylet, or can be other shapes to engage other types of styles, such as a cross-recess, a hexagonal recess, or a star recess.

The shaft 56 is conductive and, in some embodiments, can be made of a biocompatible metal, for example, stainless steel, Elgiloy, MP35N, or titanium. In other embodiments, the shaft 56 can be made of a combination of the biocompatible metal and a biocompatible polymer that is rigid at body temperature, such as polyetheretherketone (PEEK) or polyethersulfone (PES). In still other embodiments, the shaft 56 can be made of a biocompatible conductive polymer, for example a biocompatible polymer doped with a biocompatible conductive material such as carbon, titanium, platinum, or gold. The shaft 56 can be formed by, for example, molding, machining, or 3D additive manufacturing.

In some embodiments, the electrode 48 can include a cylindrical portion 98 and a conical tip 100 extending distally from the cylindrical portion 98. The conical tip 100 can have an axis B that is collinear with the longitudinal axis A of the housing lumen 62. In some embodiments, the conical tip 100 can be sharpened to enable better penetration into the tissues of the heart 16 and contact the bundle of His 26 (FIG. 1). In some embodiments, the conical tip 100 can be as short as 1 mm, 2 mm, 3 mm or 4 mm, or as long as 5 mm, 6 mm, 7 mm, or 8 mm, or any length between any two of the preceding lengths. In some embodiments, the conical tip 100 can have a length from 1 mm to 8 mm, 2 mm to 7 mm, 3 mm to 6 mm, 4 mm to 5 mm, 1 mm to 3 mm, or 2 mm to 3 mm. In some embodiments, the conical tip 100 can be about 2.5 mm long. All lengths are measured from the cylindrical portion 98 to the end of conical tip 100 along the axis B.

In some embodiments, the electrode 48 can further include an O-ring channel 102 to contain an O-ring seal 104. The electrode 48 can be disposed at the distal end 60 of the housing 52. The electrode 48 is mechanically and electrically connected to the electrode shaft portion 94. The electrode 48 can be connected to the electrode shaft portion 94 by, for example, welding, bonding with a conductive eutectic alloy, or bonding with a conductive adhesive. The O-ring channel 102 can surround the connection between the electrode 48 and the electrode shaft portion 94 so that the O-ring seal 104 can provide a liquid seal to prevent body fluids from leaking into the housing 52.

Figure 6:
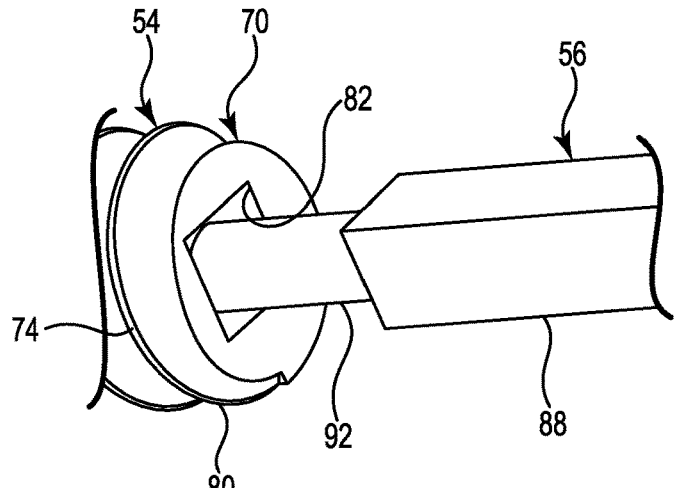
FIG. 6 is an exploded perspective view of an end of the tine assembly and a rotatable shaft of FIG. 3, according to embodiments of this disclosure.

FIG. 6 is an exploded perspective view of an end of the tine assembly 54 and the shaft 56, according to embodiments of this disclosure. As shown in the embodiment of FIG. 6, the main shaft portion 88 can have a square cross-sectional shape, while the distal shaft portion 92 can have a circular cross-sectional shape. The driver lumen 82 through the threaded portion 74 of the driver member 70 also has a square cross-sectional shape corresponding to the square cross-sectional shape of the main shaft portion 88 so that when the rotatable shaft 56 rotates, the main shaft portion 88 engages the threaded portion 74 of the driver member 70 to rotate the threaded portion 74. While the embodiment shown in FIG. 6 employs square cross-sectional shapes for the main shaft portion 88 and the driver lumen 82 through the threaded portion 74, in other embodiments, other non-circular shapes may be employed, including elliptical, rectangular, pentagonal, hexagonal, cross-recess, or star shapes.

Considering FIGS. 3-6, the fixation device 38 can be made by attaching the at least one tine 68 to the at least one lobe 84 of the carrier member 72, as described above. The hub 78 extending from the threaded portion 74 of the driver member 70 can be inserted through the carrier lumen 86. The flange 76 can be formed at an end of the hub 78 opposite the threaded portion 74, as described above, such that the carrier member 72 is rotatable about the hub 78, and the flange 76 and the threaded portion 74 restrain the axial movement of the carrier member 72. The at least one tine 68 can be inserted into the at least one slot 66 at the proximal end 58 of the housing 52 in the linear configuration. The at least one tine 68 is constrained by the housing 52 to prevent it from self-biasing back to the curved configuration. The carrier member 72 is inserted into the housing lumen 62 as the at least one lobe 84 slides within the at least one slot 66. The threaded portion 74 of the drive member 70 is threaded into the internal screw threads 64 at the proximal end 58 of the housing 52. The shaft 56 is inserted through the driver lumen 82 of the driver member 70 at the proximal end 58 of the housing 52 until the movement of the shaft 56 in the direction of the distal end 60 is limited by the narrow portion 67 of the housing lumen 62 which prevents further movement of the main shaft portion 88. The electrode 48 is connected to the electrode shaft portion 94 of the shaft 56 as described above. In some embodiments, the O-ring seal 104 is placed in the O-ring channel 102 and around the electrode shaft portion 94 before the electrode 48 is connected to the electrode shaft portion 94.

In operation, the system 10 with the lead 14 having the fixation device 38 as described above, can be used in the undeployed state shown in FIG. 3 to map one of the locations described above in reference to FIG. 1 for accessing the bundle of His 26. The electrode 48 can penetrate into the myocardium at a first spot near the bundle of His 26, measurements made, the electrode 48 quickly removed from the myocardium and moved to a second spot where the process is repeated. The actions of penetrating the myocardium with the electrode 48 by simply pushing on the lead 14 and removing the electrode 48 from the myocardium by simply pulling on the lead 14 are faster and may cause less tissue damage than the prior art which required many turns of a helical electrode to either penetrate the myocardium or remove the electrode. Thus, the present invention permits rapid and accurate mapping before positioning of the lead 14 close enough to the bundle of His 26 for efficient and effective pacing.

Once a suitable pacing location is found and the conical tip 100 of the electrode 48 has penetrated the myocardium, the fixation device 38 can be deployed to fixate the lead 14. In some embodiments, the fixation device 38 can be deployed by rotating stylet 50 in a first direction (e.g. clockwise) to rotate the shaft 56 as describe above. In other embodiments in which the electrical conductor 44 is a coil conductor, the fixation device 38 can be deployed by rotating the terminal pin 46 in the first direction to rotate the electrical conductor 44 which rotates the shaft 56.

In any case, rotating the shaft 56 in the first direction causes the tine assembly 54 to move through the housing 52 in the direction of the distal end 60. As the shaft 56 rotates, the driver member 70 also rotates as the main shaft portion 88 engages the driver lumen 82, as described above. The driver lumen 82 is sized to that the driver member 70 can slide along the shaft 56 while the main shaft portion 88 engages the driver lumen 82. The external threads 80 on the threaded portion 74 of the driver member 70 engage the internal screw threads 64 of the housing lumen 62, driving the driver member 70 toward the distal end 60. The driver member 70 pushes the carrier member 72 through the housing lumen 62, moving the attached at least one tine 68 through the at least one slot 66 to transition the at least one tine 68 from the linear configuration to the curved configuration. Because the carrier member 72 is rotatably disposed around the driver member 70, the carrier member 72 need not rotate with the driver member 70. However, frictional forces between the driver member 70 and the carrier member 72 may impart a slight rotational force on the carrier member 72. The at least one lobe 84 disposed in the at least one slot 66 prevents the carrier member 72 from rotating with the driver member 70 in response to the slight rotational force as the carrier member 72 moves through the housing lumen 62.

Figure 7:
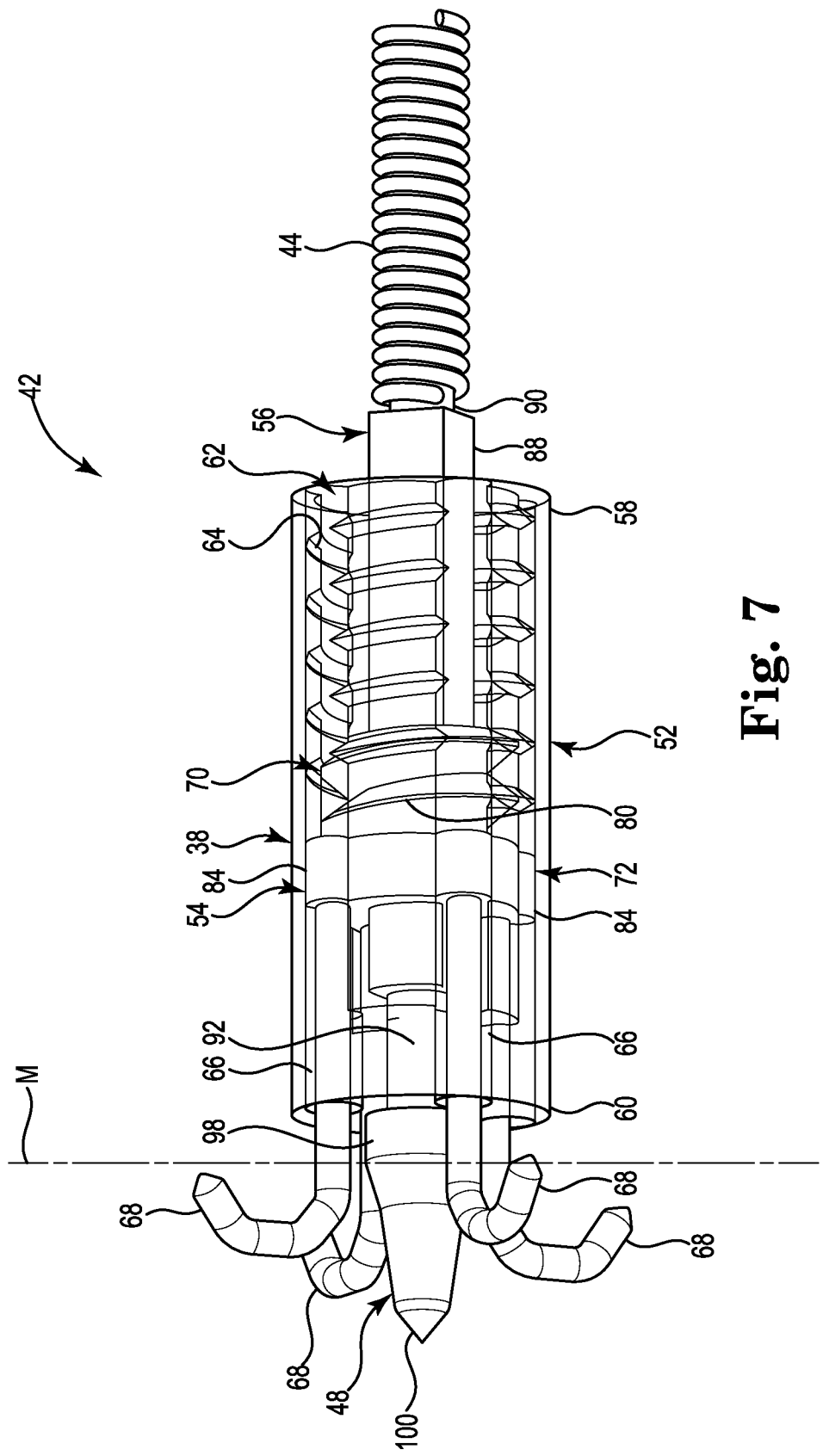
FIG. 7 is a perspective view of the device of FIG. 3 for the active fixation of the lead in a deployed state.

FIG. 7 is a perspective view of the fixation device 38 of FIG. 3 in a deployed state, according to embodiments of this disclosure. The lead body 34 is omitted for clarity. The conical tip 100 of the electrode 48 has penetrated the myocardium M (position indicated with dotted line). As each of the four tines 68 shown in FIG. 7 moves through one of the four slots 66 and begins to exit the housing 52 at the distal end 60 as they transition from the liner configuration of FIG. 3 to the curved configuration shown in FIG. 7. Each of the tines 68 penetrates the myocardium M and, unconstrained by the housing 52, self-biases to the curved configuration outside of the housing 52 as it penetrates through the myocardium, carving a curved path through the myocardium M. In the embodiment shown in FIG. 7, each of the four tines 68 is oriented to self-bias to the curved configuration in a direction curving away from the electrode 48. Other embodiments may have different orientations for the at least one tine 68. So deployed, the fixation device 38 fixates the lead 14 (FIG. 1) at the desired location.

Embodiments of the fixation device 38 may be less likely to move from the desired location than prior art devices. The electrode 48 penetrates the myocardium M before the fixation device 38 is deployed, helping to stabilize the electrode 48 during deployment, even though the electrode 48 will rotate with the shaft 56 during deployment. In addition, there should be little recoil from the force required to fixate the lead 14 because the tines 68 can deploy nearly straight out of the slots 66 and penetrate the myocardium M before substantially curving. Further, as the tines 68 deploy, they may tend to pull the electrode 48 into more secure contact with the myocardium M.

If desired, the fixation device 38 may be removed from the myocardium M by rotating the shaft 56 in a second direction opposite the first direction (e.g. counter-clockwise). Rotating the shaft 56 in the second direction causes the tine assembly 54 to move through the housing 52 in the direction of the proximal end 58. As the shaft 56 rotates, the driver member 70 rotates as the external threads 80 on the threaded portion 74 of the driver member 70 engage the internal screw threads 64 of the housing lumen 62, to drive the driver member 70 toward the proximal end 58. The driver member 70 pulls the carrier member 72 through the housing lumen 62, pulling the attached four tines 68 out of the myocardium M and back into their respective slots 66. Once the four tines 68 are out of the myocardium M, the conical tip 100 of the distal electrode can be pulled from the myocardium M to remove the fixation device 38.

Figure 8:
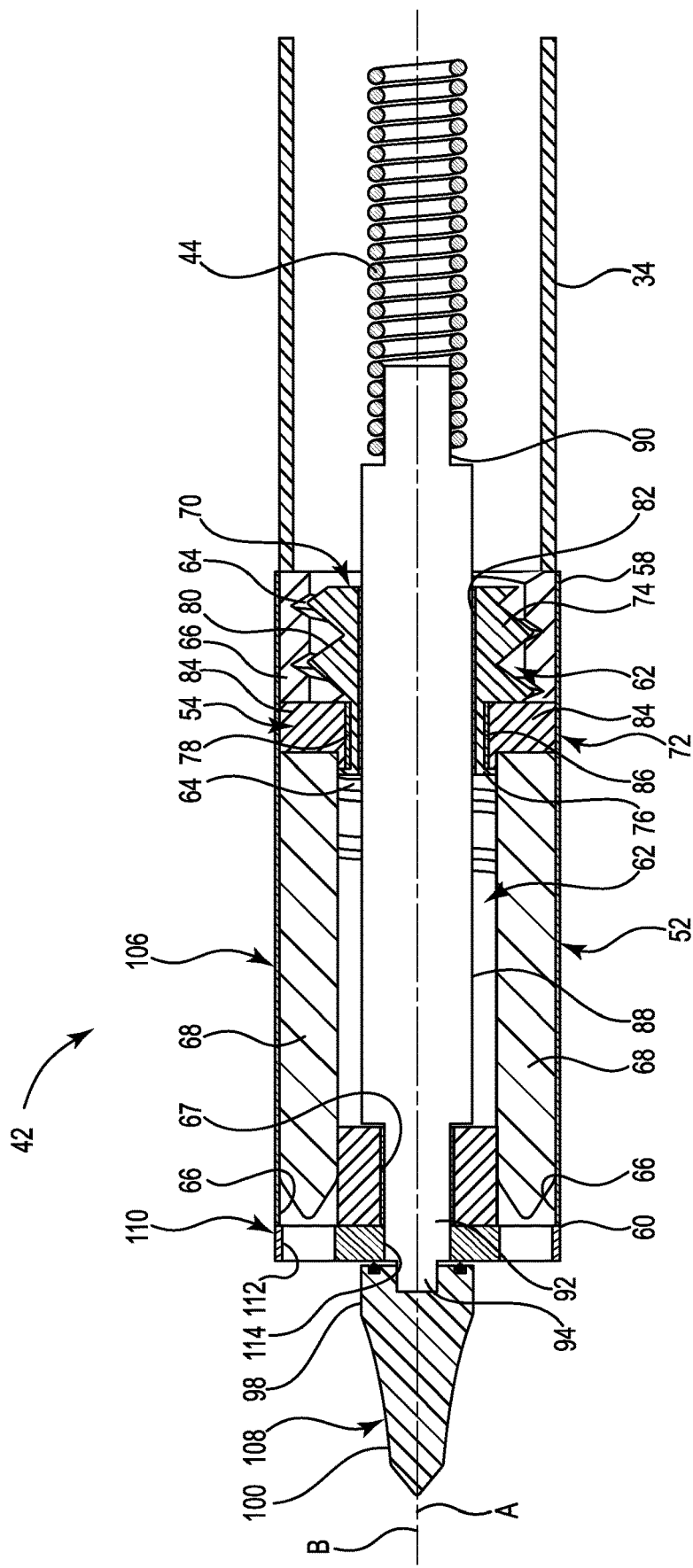
FIG. 8 is schematic cross-sectional view of a distal end of the lead of FIG. 2 including another device for the active fixation of the lead, according to embodiments of this disclosure.

FIG. 8 is schematic cross-sectional view of the distal end 42 of the lead 14 of FIG. 2 including another device for the active fixation of the lead 14, according to embodiments of this disclosure. FIG. 8 shows a fixation device 106. The fixation device 106 is substantially similar to the fixation device 38 described above in reference FIGS. 3-7, except that the electrode 48 is replaced by the electrode 108 and the O-ring seal 104 is replaced by a gasket seal 110. The electrode 108 is substantially similar to the electrode 48, except that it does not include the O-ring channel 102. The gasket seal 110 is a flat gasket defining at least one tine hole 112 (two shown) and a shaft hole 114. The at least one tine hole 112 is smaller than a diameter of the at least one tine 68 so that after the at least one tine 68 deploys, the gasket seal 110 will seal around the at least one tine 68 to prevent leakage of bodily fluids into the housing 52. In some embodiments, the at least one tine hole 112 may be only a slit in the gasket seal 110. In some other embodiments, the at least one tine hole 112 may not be formed until the at least one tine 68 deploys and punches through the gasket seal 110, forming the at least one tine hole 112. Similarly, the shaft hole 114 is smaller than a diameter of the distal shaft portion 92 will seal around the distal shaft portion 92 to prevent leakage of bodily fluids into the housing 52.

In other embodiments, the features of the embodiments of FIGS. 3 and 8 can be combined, such that electrode 48 with the O-ring channel 102 and the O-ring seal 104 is used in combination with the gasket seal 110 as described above.

Figure 9:
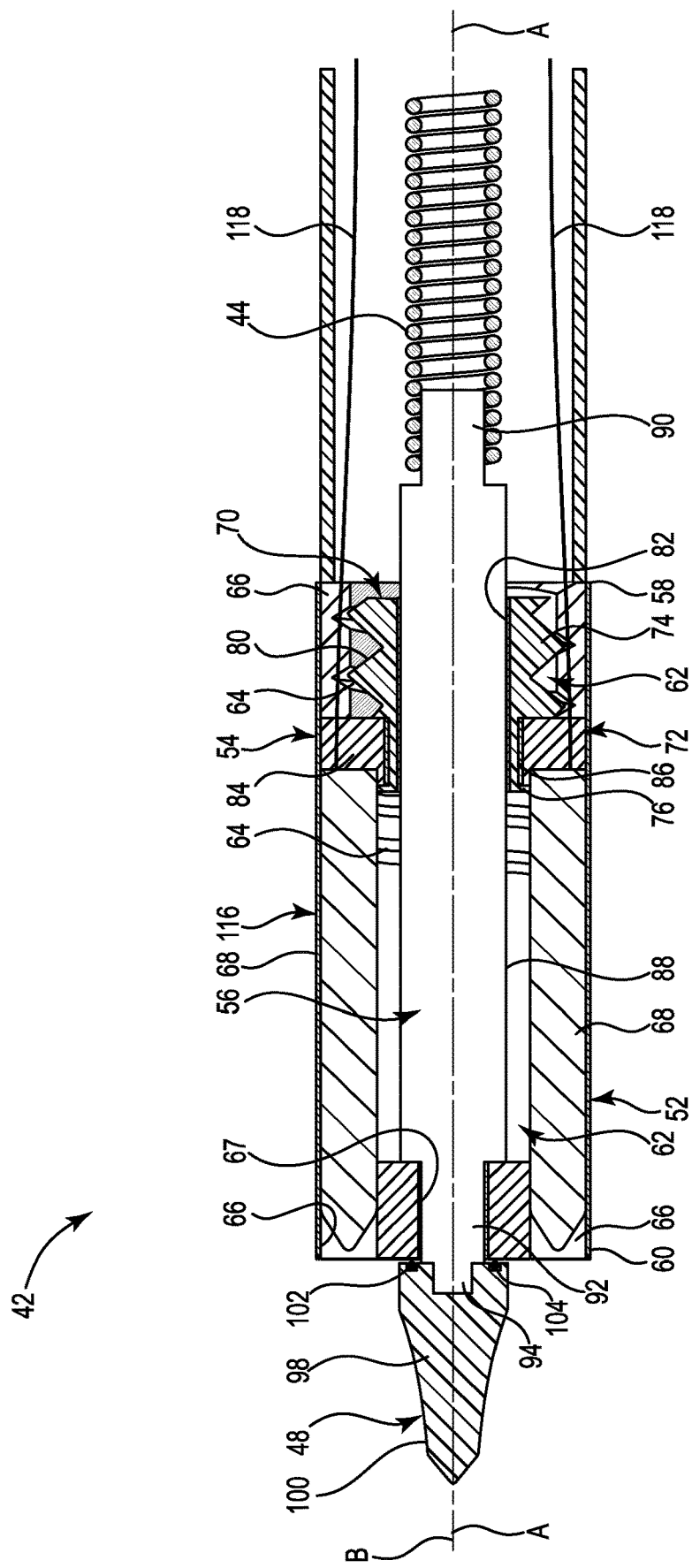
FIG. 9 is schematic cross-sectional view of a distal end of the lead of FIG. 2 including yet another device for the active fixation of the lead, according to embodiments of this disclosure.

FIG. 9 is schematic cross-sectional view of the distal end 42 of the lead 14 of FIG. 2 including another device for the active fixation of the lead 14, according to embodiments of this disclosure. FIG. 9 shows a fixation device 116. The fixation device 116 is substantially similar to the fixation device 38 described above in reference FIGS. 3-7, except that it includes at least one tine conductor 118 (two shown, four in total). The at least one tine conductor 118 extends from the connector assembly 36 (FIG. 1) to the at least one tine 68 to electrically connect the at least one tine 68 to the connector assembly 36. In such embodiments, the at least one tine 68 is electrically conductive and is electrically insulated from the electrode 48 and the shaft 56. Thus, in such embodiments, when the connector assembly 36 connects the lead 14 to the pulse generator 12 (FIG. 1), the pulse generator 12 can employ the at least one tine 68 as another pacing electrode, controlled separately from the electrode 48. In the embodiment of FIG. 9, the four tines 68 could provide four additional, individually controllable electrodes for programmable His pacing.

In the embodiments described above and shown in the FIGS. 1-9, the at least one tine 68 consists of four tines 68, the at least one slot 66 consisted of four slots 66, the at least one lobe 84 consisted of four lobes 84, and the at least one tine conductor 118 consisted of four tine conductors 118. However, it is understood that embodiments can include only a single tine 68 or a plurality of tines 68, including 2, 3, 5, 6, 7, 8, 9, or 10 or more tines 68. It is further understood that embodiments can include only a single slot 66 or a plurality of slots 66, so long as the number of slots 66 is at least equal to the number of tines 68. It is further understood that embodiments can include only a single lobe 84 or a plurality of lobes 84. It is further understood that embodiments can include only a single tine conductor 118 or a plurality of tine conductors 118.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A device for the active fixation of an implantable medical lead into tissue, the device comprising:
    a housing including a proximal end for connecting to the lead and a distal end opposite the proximal end, the housing defining a housing lumen having a longitudinal axis extending between the proximal end and the distal end, the housing including a plurality of longitudinal slots disposed radially outward of the housing lumen;
    a tine assembly including a carrier member partially disposed within the housing lumen, and a plurality of tines coupled to the carrier member, each of the tines disposed within a respective one of the longitudinal slots and configured to self-bias from a linear configuration within the housing to a curved configuration outside of the housing, wherein the carrier member includes a lobe at an outer circumference of the carrier member, the lobe configured to engage one of the plurality of longitudinal slots to prevent rotation of the carrier member relative to the housing while permitting the carrier member to move axially through the housing lumen, wherein one of the plurality of tines is connected to and projects from the lobe;
    a rotatable shaft extending through the housing lumen, the shaft having a proximal end and a distal end and being configured to engage the carrier member such that rotation of the shaft causes longitudinal movement of each of the tines relative to the housing; and
    a conical tip electrode attached to the distal end of the rotatable shaft.

2. The device of claim 1, wherein rotation of the shaft in a first direction moves each of the plurality of tines out of the housing and to allow each of the plurality of tines to transition from the linear configuration to the curved configuration.

3. The device of claim 2, wherein rotation of the shaft in a second direction opposite the first direction retracts each of the plurality of tines relative to the housing and causes transition the at least one tine from the curved configuration to the linear configuration to release the lead from tissue.

4. The device of claim 1, wherein the conical tip electrode has an axis that is collinear with the longitudinal axis of the housing lumen.

5. The device of claim 4, wherein the shaft is electrically and mechanically connected to the conical tip electrode.

6. The device of claim 5, wherein the conical tip electrode is configured to rotate with the shaft.

7. The device of claim 6, wherein the conical tip electrode further comprises an O-ring seal configured to provide a liquid seal between the conical tip electrode and the housing.

8. The device of claim 1, wherein the housing further includes internal screw threads extending along the housing lumen, and the tine assembly further includes:
    a driver member disposed within the housing lumen, the driver member defining a driver lumen coaxial with the housing lumen, the driver member including:
        a threaded portion having external screw threads engaged with the internal screw threads of the housing;
        a flange; and
        a hub connecting the flange to the threaded portion.

9. The device of claim 8, wherein the rotatable shaft extends through the driver lumen, the shaft configured to engage the driver member such that rotation of the shaft rotates the driver member.

10. The device of claim 8, wherein the flange and the threaded portion of the driver member constrain axial movement of the carrier member.

11. The device of claim 8, wherein each of the plurality of slots extends from the proximal end of the housing to the distal end of the housing and parallel to the longitudinal axis.

12. The device of claim 11, wherein the carrier member includes a plurality of lobes each configured to engage one of the plurality of slots to prevent axial rotation of the carrier member relative to the housing while permitting the carrier member to move through the housing lumen while the shaft rotates the driver member, wherein each of the plurality of tines is connected to and projects from a respective one of the plurality of lobes.

13. The device of claim 8, wherein the driver lumen is sized so that the driver member can slide along the shaft while the shaft rotates the driver member.

14. An implantable medical lead comprising:
a flexible, tubular lead body including a proximal end and a distal end;
a connector assembly connector disposed at the proximal end;
an electrical conductor extending through the tubular body from the connector assembly to the distal end; and
a device for the active fixation of the implantable medical lead, the device disposed at the distal end of the lead, the device including:
- a housing including a proximal end connected to the distal end of the lead body, and a distal end opposite the proximal end of the housing, the housing defining a housing lumen having a longitudinal axis extending between the proximal end of the housing and the distal end of the housing, the housing including a plurality of longitudinal slots disposed radially outward of the housing lumen;
- a tine assembly including a carrier member partially disposed within the housing lumen, and a plurality of tines coupled to the carrier member, each of the tines disposed within a respective one of the longitudinal slots and configured to self-bias from a linear configuration within the housing to a curved configuration outside of the housing, wherein the carrier member includes a lobe at an outer circumference of the carrier member, the lobe configured to engage one of the plurality of longitudinal slots to prevent rotation of the carrier member relative to the housing while permitting the carrier member to move axially through the housing lumen, wherein one of the plurality of tines is connected to and projects from the lobe;
- a rotatable shaft extending through the housing lumen, the shaft having a proximal end and a distal end and being configured to engage the carrier member such that rotation of the shaft causes longitudinal movement of each of the tines relative to the housing; and
- a conical tip electrode attached to the distal end of the rotatable shaft.

15. The lead of claim 14, wherein at least one of the tines is conductive and electrically insulated from the electrode and the shaft.

16. The lead of claim 15, further including at least one tine conductor extending through the tubular body from the connector assembly to the at least one of the tines that is conductive.

* * * * *